United States Patent
Krieg et al.

(10) Patent No.: US 9,095,263 B2
(45) Date of Patent: Aug. 4, 2015

(54) PATIENT COUCH

(71) Applicants: Tobias Krieg, Pullenreuth (DE); Michael Meyer, Hausen (DE)

(72) Inventors: Tobias Krieg, Pullenreuth (DE); Michael Meyer, Hausen (DE)

(73) Assignee: Siemens Aktiengesellschaft, München (DE)

( * ) Notice: Subject to any disclaimer, the term of this patent is extended or adjusted under 35 U.S.C. 154(b) by 0 days.

(21) Appl. No.: 13/974,502

(22) Filed: Aug. 23, 2013

(65) Prior Publication Data

US 2014/0053333 A1 Feb. 27, 2014

(30) Foreign Application Priority Data

Aug. 23, 2012 (DE) .......................... 10 2012 215 016

(51) Int. Cl.
A47B 13/00 (2006.01)
A61B 6/04 (2006.01)
A61B 6/00 (2006.01)

(52) U.S. Cl.
CPC ............... *A61B 6/0442* (2013.01); *A61B 6/487* (2013.01)

(58) Field of Classification Search
CPC ...... A61B 5/0555; A61B 6/032; A61B 5/055; A61B 6/4417; A61B 5/0035; A61B 5/4528; A61B 6/5247; A61B 8/4416; A61G 13/08; A61G 15/02; A61G 7/015; A61N 5/10; A61N 2005/1059; A61N 5/1048; A61F 5/37; E05D 7/0009; E05D 7/04; E05D 7/0415; Y10T 16/529; Y10T 16/532; Y10T 16/5324
USPC ...................... 5/601, 610, 611, 613, 616–618; 378/208, 209; 108/69, 77, 80–82; 403/59, 84, 85, 91
See application file for complete search history.

(56) References Cited

U.S. PATENT DOCUMENTS

| | | | | |
|---|---|---|---|---|
| 3,532,882 A | * | 10/1970 | Craig et al. ........................ | 5/611 |
| 3,724,004 A | * | 4/1973 | Behrens ............................ | 5/611 |
| 4,101,120 A | * | 7/1978 | Seshima ........................... | 5/616 |
| 4,452,439 A | * | 6/1984 | Hogan .............................. | 5/601 |
| 5,131,105 A | * | 7/1992 | Harrawood et al. .............. | 5/607 |
| 5,157,787 A | * | 10/1992 | Donnellan et al. ................ | 5/610 |
| 5,205,004 A | * | 4/1993 | Hayes et al. ...................... | 5/611 |
| 5,628,078 A | * | 5/1997 | Pennington et al. ............. | 5/618 |
| 6,378,149 B1 | * | 4/2002 | Sanders et al. ................... | 5/624 |
| 6,615,428 B1 | * | 9/2003 | Pattee ............................... | 5/601 |
| 6,615,429 B2 | * | 9/2003 | Weil et al. ......................... | 5/601 |
| 6,640,363 B1 | * | 11/2003 | Pattee et al. ..................... | 5/601 |
| 6,681,423 B2 | * | 1/2004 | Zachrisson ....................... | 5/610 |
| 2007/0214570 A1 | * | 9/2007 | Coppens et al. .................. | 5/601 |
| 2014/0109316 A1 | * | 4/2014 | Jackson et al. ................... | 5/601 |

FOREIGN PATENT DOCUMENTS

DE     93 06 150 U1     7/1993
DE     10 2004 013 585 A1     10/2005

OTHER PUBLICATIONS

German Office Action dated Jun. 20, 2013 for corresponding German Patent Application No. DE 10 2012 215 016.1 with English translation.

* cited by examiner

*Primary Examiner* — Timothy D Collins
*Assistant Examiner* — Richard G Davis
(74) *Attorney, Agent, or Firm* — Lempia Summerfield Katz LLC

(57) ABSTRACT

A patient couch for a medical diagnosis and/or treatment device includes a metal-free fluoroscopy section and at least two couch sections that are connected to each other in an articulated manner and may be pivoted relative to each other using a motor-driven adjustment mechanism. The adjustment mechanism is arranged outside of the metal-free fluoroscopy section.

14 Claims, 4 Drawing Sheets

PATIENT COUCH

This application claims the benefit of DE 10 2012 215 016.1, filed on Aug. 23, 2012, which is hereby incorporated by reference.

BACKGROUND

The present embodiments relate to a patient couch for a medical diagnosis and/or treatment device.

Medical diagnosis and/or treatment devices may have different patient tables. There are patient tables having a one-piece couch that have an extremely high load-bearing capacity and offer optimal x-ray transparency. However, patient couches of this type only allow the patient to adopt a flat supine or prone position. If the patient is placed in a side position, accessibility for the user is more difficult.

In addition, extremely adaptable operating tables in which good flexibility with regard to the positioning of the patient is paramount are known. Due to the design concept, however, operating tables of this type have a complex construction, and disadvantages in terms of fluoroscopic suitability are to be accepted.

In practice, one-piece patient tables or patient couches may be used when only angiographic examinations are to be performed for diagnostic purposes. If interventional treatments are also to be possible, an operating table having a complex structure is provided. Apart from the flexibility with regard to the positioning of the patient, this has disadvantages in terms of fluoroscopic suitability and due to the complicated design.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a patient couch that is simple in design and is suitable for the performance of interventional treatments is provided.

An adjustment mechanism of a patient couch is arranged outside of the fluoroscopy section.

The patient couch according to one or more of the present embodiments has the advantage that the entire couch surface enables good fluoroscopy. For this purpose, the adjustment mechanism is arranged outside of the fluoroscopy section and consequently at the side of the patient couch or at the side on the couch sections.

In the patient couch according to one or more of the present embodiments, the adjustment mechanism may allow a relative rotation of the two adjustable couch sections from −20° to +20°. This enables the patient to be positioned in different ways, with the result that suitable positioning of the patient is possible for all relevant diagnoses and/or interventions.

In one embodiment, a first couch section is arranged on a height-adjustable pedestal, and an angle of inclination of the first couch section is selectable. The height adjustability provided also increases accessibility to the patient, enabling the user to perform the diagnosis or the intervention more easily.

In the patient couch, an adjustment mechanism may be arranged on each of the two sides of the couch sections. Because the adjustment mechanisms are arranged to the side of the fluoroscopy section, the fluoroscopy section may be implemented in a completely metal-free design. This provides that no interference caused by metal parts may occur.

One embodiment of the patient couch provides that the adjustment mechanism includes a linear actuator that is arranged on the first couch section and engages with a lever spaced at a distance from the axis of rotation of the second couch section. The linear actuator has an extendable piston rod or the like that acts with a free end on a lever or a lever section of the second couch section, such that the second couch section may be pivoted about the axis of rotation. Due to the coupling of the linear actuator with the lever or lever section, the second couch section is able to be pivoted out of a horizontal rest position both in a clockwise direction and in an anticlockwise direction.

The actuator may have a rounded end section that is matched to fit a corresponding section of the lever that has a mirror-identical shape. In this way, a force- and form-fit coupling is produced during the adjustment of the second couch section.

Alternatively, the patient couch according to one or more of the present embodiments may also be embodied such that the adjustment mechanism is embodied as a worm gear or includes a worm gear. In one embodiment, the adjustment mechanism may include a geared motor having a planetary gear as the first reduction stage. Using the planetary gear, the high motor rotation speed is translated to a lower output speed, with the required torque being generated by the worm gear in a second reduction stage.

In this embodiment of the patient couch, a spring-operated brake and/or an incremental encoder may be provided in addition.

DETAILED DESCRIPTION

Figure 1:
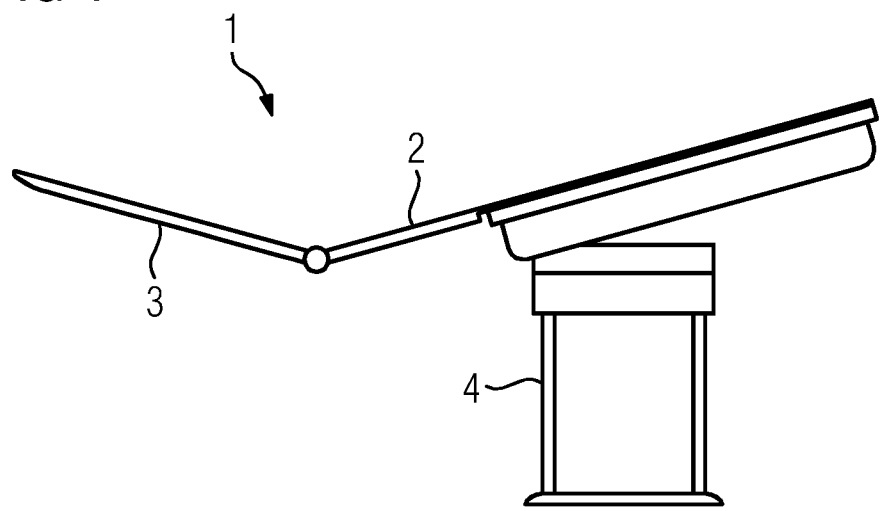
FIG. 1 shows a side view of one embodiment of a patient couch.
Figure 2:
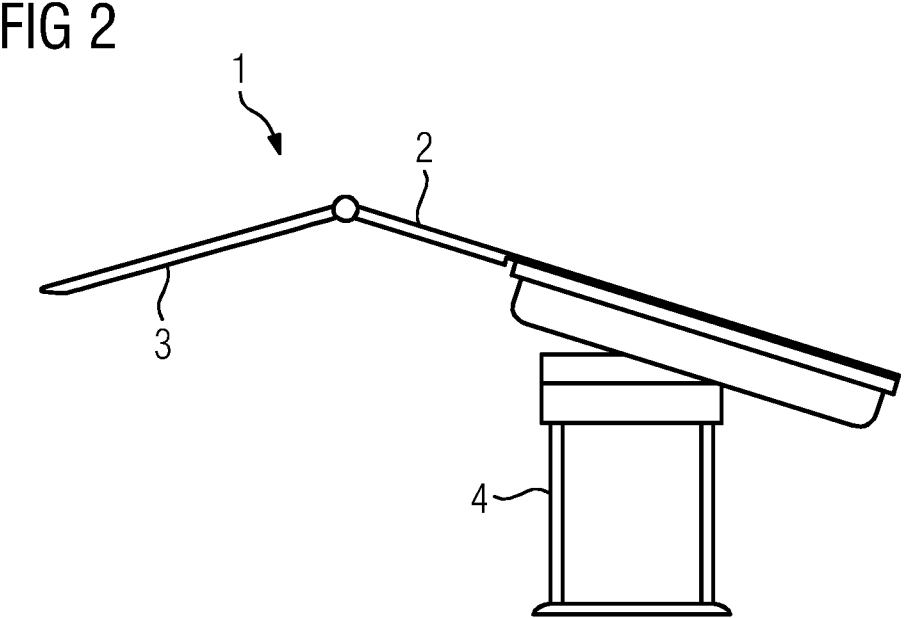
FIG. 2 shows the patient couch of FIG. 1 in a different position.

FIGS. 1 and 2 show one embodiment of a patient couch 1. The patient couch 1 is provided for a medical diagnosis and/or treatment device. The patient couch 1 has a first couch section 2 and a second couch section 3 (e.g., two couch sections) that are connected to each other in an articulated manner. The two couch sections 2, 3 may be pivoted relative to each other using a motor-driven adjustment mechanism.

The first couch section 2 is arranged on a height-adjustable pedestal 4, enabling the patient couch 1 to be positioned at a comfortable height for a user.

FIG. 1 shows a position of the patient couch in which the second couch section 3 is offset upward at an angle relative to the first couch section 2. In contrast, FIG. 2 shows a position of the patient couch 1 in which the second couch section 3 is offset downward at an angle relative to the first couch section 2.

The patient couch 1 is suitable for performing medical diagnoses using angiography. In addition, the patient couch 1 may be used for interventional treatments. Because the two couch sections 2, 3 may be flexibly adjusted and because, for example, a specific relative position may be set, the position may account for a lordotic curvature of the patient's spine, for example. In the case of conventional patient tables, this may only be achieved by the patient adopting a side position and drawing up his/her legs. FIGS. 1 and 2 show that the first couch section 2 may be pivoted about an axis of rotation 5 relative to the pedestal 4.

Figure 3:
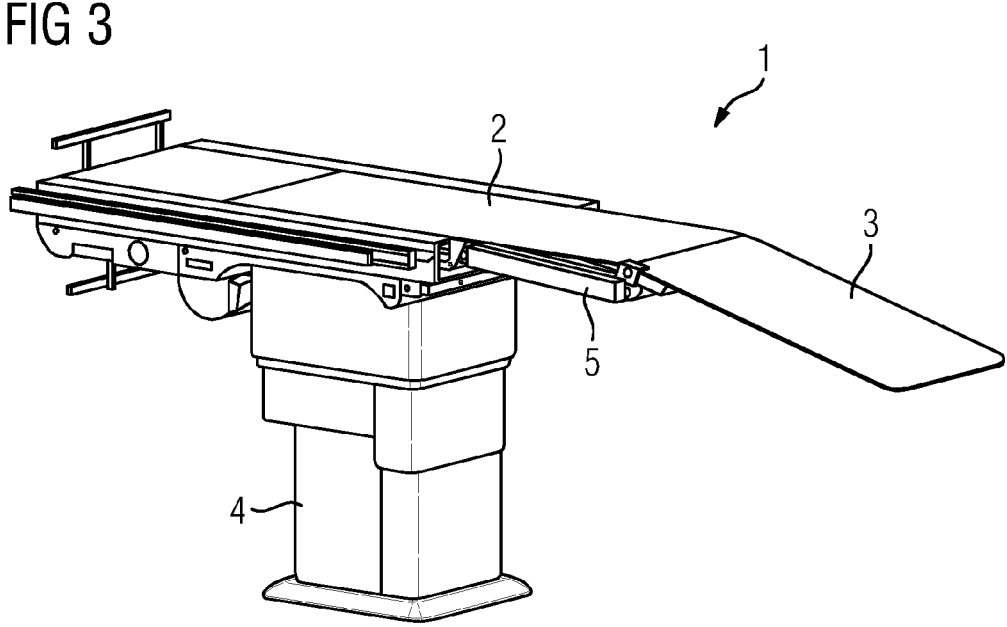
FIG. 3 shows a perspective view of one embodiment of a patient couch.

FIG. 3 shows the patient couch 1 in a perspective view. The first couch section 2 and the second couch section 3 have a metal-free fluoroscopy section, and the adjustment mechanism 5 is attached at each of the two opposing sides, thereby enabling the intermediate fluoroscopy section to be implemented in a completely metal-free design.

Figure 4:
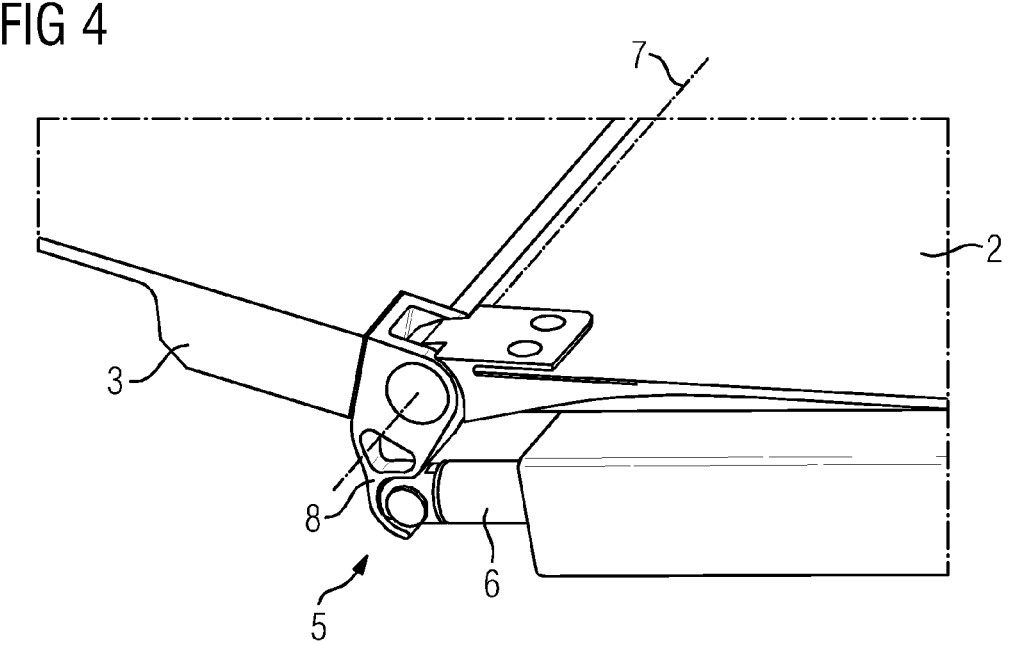
FIG. 4 shows a magnified view of the patient couch of FIG. 3 in the region of an adjustment mechanism.
Figure 5:
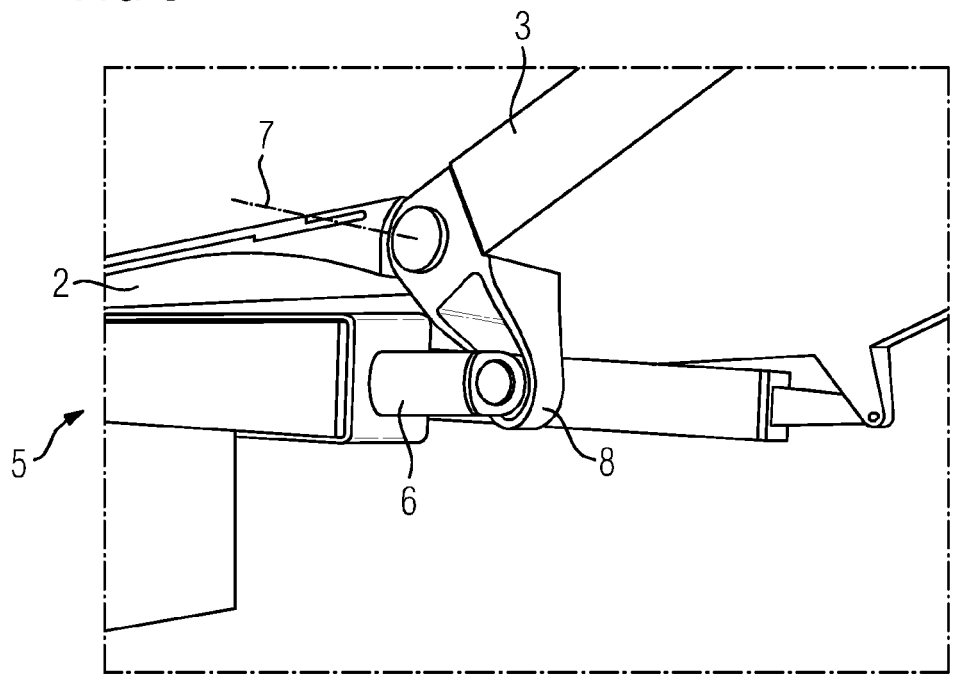
FIG. 5 shows another view of the adjustment mechanism.

The patient couch 1 shown in FIG. 3 has a lever mechanism that is shown in detail in FIGS. 4 and 5.

The adjustment mechanism 5 includes a linear actuator 6 that is arranged on the first couch section 2 and engages with a lever 8 that is spaced at a distance from an axis of rotation 7 of the second couch section 3. FIG. 4 shows that the actuator 6 has a round end section that is matched to fit a corresponding section of the lever 8 that has a mirrored shape (e.g., mirror-identical shape), such that the second couch section 3 may be pivoted by extending or retracting a piston rod of the actuator 6.

FIG. 5 shows the adjustment mechanism from a different perspective. The adjustment mechanism 5 is provided on each of two sides of the first couch section 2, thereby enabling the second couch section 3 to be pivoted by parallel forces.

Figure 6:
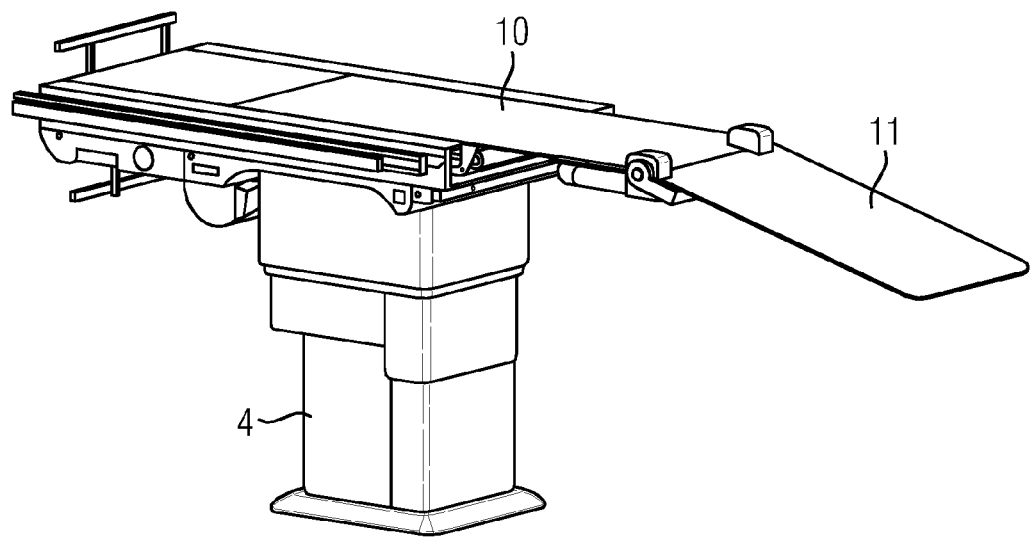
FIG. 6 shows a second exemplary embodiment of a patient couch with a worm gear.
Figure 7:
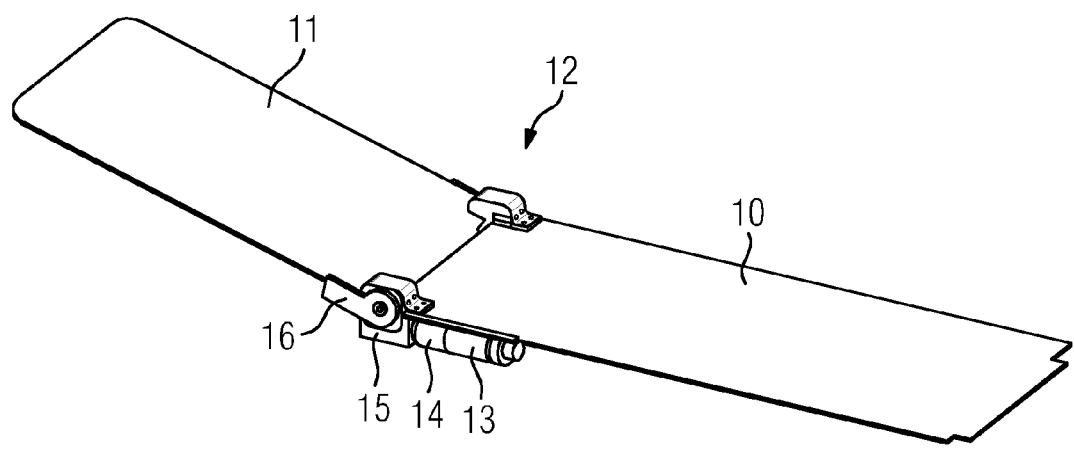
FIG. 7 shows a magnified view of the patient couch of FIG. 6.

FIGS. 6 and 7 show a second exemplary embodiment of a patient couch 9, the design of which corresponds substantially to the patient couch 1 of the first exemplary embodiment. The patient couch 9 includes a first couch section 10 that is pivotably mounted on a pedestal 4, and a second couch section 11 that is connected in an articulated manner to the first couch section 10. In this exemplary embodiment, the range of movement of the second couch section 11 extends from approximately −20° to +90°. In FIG. 6, the angular position −15° is shown by way of example.

FIG. 7 shows the couch sections 10, 11 of the patient couch 9 on an enlarged scale. The adjustment mechanism 12 is embodied differently from the previous exemplary embodiment and includes a motor 13 to which a planetary gear 14 is flange-mounted as a first reduction stage, by which the comparatively high rotational speed of the motor 13 is reduced. A worm gear 15 that is driven by the planetary gear 14 is provided as the second reduction stage. The worm gear 15 includes a worm gear shaft that drives a worm wheel that effects the adjustment of the second couch section 11 by way of a connecting element 16.

The adjustment mechanism has a spring-operated brake and an incremental encoder.

Although the invention has been illustrated and described in detail on the basis of the preferred exemplary embodiment, it is not limited by the disclosed examples and other variations can be derived herefrom without leaving the scope of protection of the invention.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A patient couch for a medical diagnosis, treatment, or medical diagnosis and treatment device, the couch comprising:
    a metal-free fluoroscopy section; and
    at least two couch sections that are connected to each other in an articulated manner and are pivotable relative to each other using an adjustment mechanism that is motor-driven,
    wherein the adjustment mechanism is arranged outside of the metal-free fluoroscopy section,
    wherein the adjustment mechanism includes a linear actuator that is arranged on a first couch section of the at least two couch sections and engages with a lever that is spaced at a distance from an axis of rotation of a second couch section of the at least two couch sections, and
    wherein the linear actuator has a rounded, convex end section that is matched to fit a corresponding concave section of the lever, providing a male-female connection arrangement.

2. The patient couch as claimed in claim 1, wherein the adjustment mechanism allows a relative rotation of the at least two couch sections from −20° to +20°.

3. The patient couch as claimed in claim 2, wherein the first couch section of the at least two couch sections is arranged on a height-adjustable pedestal, and
    wherein an inclination of the first couch section is selectable.

4. The patient couch as claimed in claim 2, further comprising another adjustment mechanism,
    wherein the adjustment mechanism is arranged on one of two sides of the couch sections, and
    wherein the other adjustment mechanism is arranged on the other of the two sides of the couch sections.

5. The patient couch as claimed in claim 1, wherein the first couch section of the at least two couch sections is arranged on a height-adjustable pedestal, and
    wherein an inclination of the first couch section is selectable.

6. The patient couch as claimed in claim 5, further comprising another adjustment mechanism,
    wherein the adjustment mechanism is arranged on one of two sides of the couch sections, and
    wherein the other adjustment mechanism is arranged on the other of the two sides of the couch sections.

7. The patient couch as claimed in claim 5, wherein the adjustment mechanism includes a worm gear.

8. The patient couch as claimed in claim 7, wherein the adjustment mechanism includes a geared motor having a planetary gear.

9. The patient couch as claimed in claim 7, wherein the adjustment mechanism has a spring-operated brake, an incremental encoder, or the spring-operated brake and the incremental encoder.

10. The patient couch as claimed in claim 1, further comprising another adjustment mechanism,
    wherein the adjustment mechanism is arranged on one of two sides of the couch sections, and
    wherein the other adjustment mechanism is arranged on the other of the two sides of the couch sections.

11. The patient couch as claimed in claim 1, wherein the adjustment mechanism includes a worm gear.

12. The patient couch as claimed in claim 11, wherein the adjustment mechanism includes a geared motor having a planetary gear.

13. The patient couch as claimed in claim 12, wherein the adjustment mechanism has a spring-operated brake, an incremental encoder, or the spring-operated brake and the incremental encoder.

14. The patient couch as claimed in claim 11, wherein the adjustment mechanism has a spring-operated brake, an incremental encoder, or the spring-operated brake and the incremental encoder.

* * * * *